United States Patent [19]

Gardner et al.

[11] 4,048,238

[45] Sept. 13, 1977

[54] PROMOTED LIQUID PHASE OXIDATION OF ALKYL AROMATIC COMPOUNDS

[75] Inventors: Lloyd E. Gardner; Darryl R. Fahey; John E. Mahan, all of Bartlesville, Okla.

[73] Assignee: Phillips Petroleum Company, Bartlesville, Okla.

[21] Appl. No.: 620,464

[22] Filed: Oct. 7, 1975

[51] Int. Cl.$^2$ .................... C07C 27/12; C07C 29/00
[52] U.S. Cl. ................... 260/618 R; 260/524 R; 260/524 N; 260/599; 260/650 R; 260/651 R; 560/241
[58] Field of Search ............ 260/488 CD, 618 R, 599, 260/524 N, 524 R

[56] References Cited

U.S. PATENT DOCUMENTS

| | | | |
|---|---|---|---|
| 2,643,269 | 6/1953 | Augustine | 260/590 |
| 2,648,638 | 8/1953 | Richter et al. | 252/439 |
| 3,310,581 | 3/1967 | Mares | 260/524 |
| 3,349,117 | 10/1967 | Selwitz et al. | 260/488 CD |
| 3,644,543 | 2/1972 | Notaro et al. | 260/650 R |
| 3,665,030 | 5/1972 | d'Ostrowick et al. | 260/618 R |
| 3,715,388 | 2/1973 | Valbert | 260/497 R |
| 3,715,389 | 2/1973 | Hoch et al. | 260/497 R |
| 3,772,383 | 11/1973 | Kominami et al. | 260/488 CD |
| 3,780,094 | 12/1973 | Herz | 260/488 CD |
| 3,867,430 | 2/1975 | Grozhan et al. | 260/618 R |

Primary Examiner—Norman Morgenstern

[57] ABSTRACT

A process is provided for oxygenating alkyl-substituted aromatic compounds. In the process alkyl-substituted aromatic compounds are contacted with molecular oxygen in the presence of a suitable monocarboxylic acid, an at least partially soluble Te or Se compound, an inorganic bromine compound, and a compound selected from inorganic nitrates and compounds convertible to inorganic nitrates at conditions of the process. In an embodiment of the invention the process is carried out in two distinct steps with contact of the alkyl-substituted aromatic compounds and oxygen in the presence of the essential components produce an ester comprising both an aromatic alcohol and the carboxylic acid with subsequent hydrolyzing of this ester to produce an aromatic alcohol with regeneration of the carboxylic acid.

10 Claims, 1 Drawing Figure

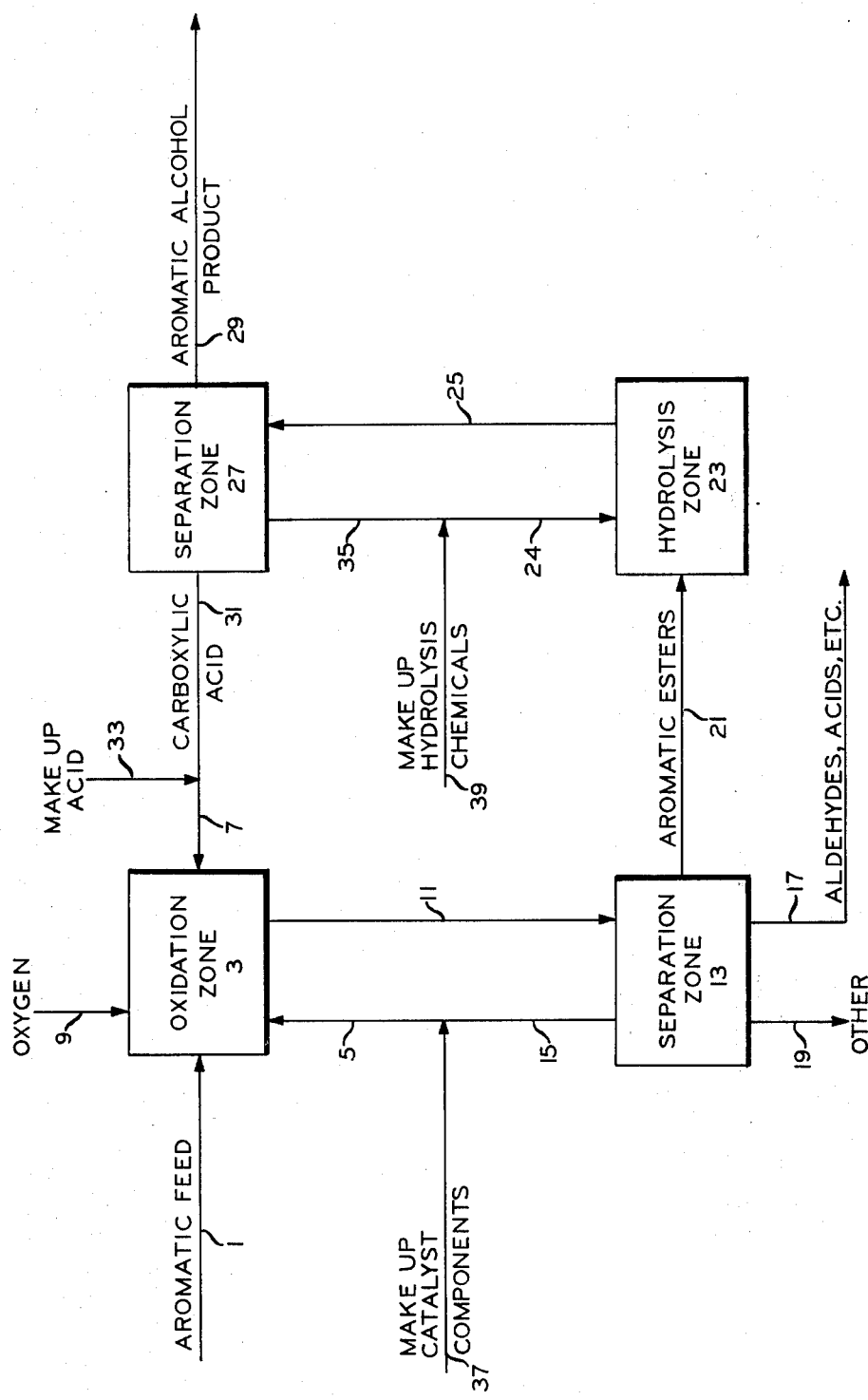

PROMOTED LIQUID PHASE OXIDATION OF ALKYL AROMATIC COMPOUNDS

BACKGROUND OF THE INVENTION

This invention relates to the oxidation of hydrocarbons. In one of its aspects this invention relates to the oxidation of alkyl-substituted hydrocarbons. In still another of its aspects this invention relates to liquid phase processes for the oxidative conversion of alkyl-substituted aromatic compounds to oxygen-containing products. In yet another aspect it relates to the production of oxidation products such as aromatic alcohols, aldehydes, and esters.

It has theretofore been known that relatively plentiful hydrocarbons can be converted to other less plentiful and therefore more valuable organic compounds by processes such as oxidation. For example, alkyl-substituted hydrocarbons such as toluene have been converted to oxygenated products such as benzaldehyde in vapor phase oxidation processes using various catalyst systems.

The present invention provides a liquid phase process for the oxidative conversion of alkyl-substituted aromatic compounds to oxygen-containing products which can be used as an alternative process to those already known. The process is particularly applicable for producing products in an intermediate stage of oxidation such as aromatic alcohols, aldehydes, and esters. The process employs the presence of a monocarboxylic acid, hence the alcohol products are obtained principally in the form of esters of the carboxylic acid. If desired, the esters can be readily hydrolyzed to liberate the alcohols, and the monocarboxylic acid can be recycled.

It is an object of this invention to provide a method for producing oxidation products from the conversion of alkyl-substituted aromatics.

Other objects, aspects and the advantages of this invention will become apparent upon reading the specification and the appended claims.

STATEMENT OF THE INVENTION

According to the process of the present invention, an alkyl-substituted aromatic compound is converted to oxygenated products in a liquid phase operation by contacting the alkyl-substituted aromatic compound with molecular oxygen in the presence of a suitable monocarboxylic acid, a minor amount of at least a partially soluble tellurium or selenium compound, a minor amount of a suitable inorganic bromide compound, and a minor amount of a suitable inorganic nitrate compound or a compound convertible to a nitrate under conditions of the reaction. Optionally, the reaction can be carried out in the additional presence of minor amounts of water or acetic anhydride.

In one embodiment of the present invention, alkyl-substituted aromatic compounds are converted to the corresponding aromatic alcohols in a multi-step process comprising, as a first step, reacting a suitable aromatic feed compound with molecular oxygen, a monocarboxylic acid, a soluble tellurium or selenium compound, an inorganic bromide compound, and an inorganic nitrate compound, optionally in the presence of water or acetic anhydride, to produce an ester of an aromatic alcohol and of the carboxylic acid; and, as a second step, hydrolyzing the ester from step 1 to produce an aromatic alcohol product and to regenerate the monocarboxylic acid for recycle to step 1.

The alkyl-substituted aromatic compounds which can be used as feedstocks for the present invention are those aromatic compounds with oxidizable alkyl substituents. Generally these compounds will correspond to the following generic formulas

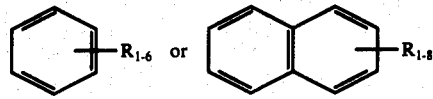

wherein each R is selected from branched or unbranched alkyl groups having from one to about 6 carbon atoms, more usually from 1 to about 4 carbon atoms, or halogen atoms, at least one R being an alkyl group free of quaternary carbon atoms. Usually, such compounds will contain 1-2 alkyl groups and 0-1 halogen atoms.

Some examples of such suitable feedstocks are: toluene, p-tert-butyltoluene, o-xylene, m-xylene, p-xylene, 1,2,4-trimethylbenzene, 1,3,5-trimethylbenzene, 1,2,4,5-tetramethylbenzene, p-chlorotoluene, ethylbenzene, p-isopropyltoluene, isopropylbenzene, n-butylbenzene, p-propyltoluene, m-bromotoluene, α-methylnaphthalene, β-isopropylnaphthalene, n-hexylbenzene, and the like, and mixtures thereof.

The carboxylic acids which are suitable for use in the present invention process are those alkanoic acids having from 1 to about 6 carbon atoms per molecule. Some examples of these are formic acid, acetic acid, propionic acid, butyric acid, 3-methylbutyric acid, pentanoic acid, hexanoic acid, and the like, and mixtures thereof. Acetic acid is particularly effective and convenient.

The soluble tellurium and selenium compounds which are used in the catalyst system of the present invention are those which have a significant solubility in the reaction mixture under conditions of the oxidative conversion. As a practical matter, the compounds which are most useful are tellurium dioxide, tellurium tetrabromide, and selenium dioxide. Of these, the tellurium oxide is presently considered most effective and convenient.

The inorganic bromide components which are used in the catalyst system of the present invention include the alkali metal bromides and hydrogen bromide. Of these, lithium bromide has been found particularly effective. When tellurium bromide is utilized as the tellurium component, this same compound can also satisfy the inorganic bromide requirement.

The inorganic nitrate components which are suitable for use in the catalyst system of the present invention include the alkali metal nitrates and nitric acid. Also included are compounds which are convertible to inorganic nitrates under the oxidative conditions of the invention process. Some of these are alkali metal nitrates, and oxides of nitrogen such as NO, $NO_2$, and the like. Alkali metal nitrates such as lithium nitrate have been found particularly convenient and effective.

The conditions under which the oxidation process of the present invention is carried out are those conditions of temperature and pressure under which the reaction mixture is substantially in the liquid phase. Generally the temperature is maintained in the range of about 50° to about 200° C, more usually about 150° to about 170° C. The partial pressure of oxygen in the system will generally be in the range of about 5 to about 500 psig ($3.4 \times 10^4 - 3.4 \times 10^6$ Pa), more usually about 10 to about 100 psig (6.9 × 10⁴ − 6.9 × 10⁵ Pa). Air can be used as the source of oxygen, if desired, or the molecular oxygen can be diluted with nitrogen or with other inert gases. The amount of oxygen present within the reaction zone will, in any event, be at least the theoretical amount to oxidize the alkyl groups present to the extent desired and will generally be in excess of that theoretical amount. The process can be carried out either batchwise or continuously and the reaction time will depend on the specific components of the reaction mixture but will generally be in the range of about 0.1 to about 30 hours, more frequently about 0.5 to about 4 hours.

The other components of the reaction mixture will generally be present in amounts as shown in the following table. The amounts are in terms of moles (or millimoles) per mole of alkyl-substituted aromatic feedstock. Tellurium, selenium, bromide and nitrate compounds are calculated in terms of their ions.

matic alcohols, leave process via line 17. Other products, generally heavier, pass from the process via line 19.

Aromatic esters pass via line 21 into hydrolysis zone 23 where they contact hydrolysis chemicals such as catalyst and water entering via line 24. The reaction mixture from hydrolysis zone 23 is passed via line 25 into separation zone 27 from which aromatic alcohol product is removed via line 29. Liberated carboxylic acid is recycled to oxidation zone 3 via line 31 and line 7. Unconverted aromatic ester and recycle hydrolysis chemicals return to hydrolysis zone 23 via line 35. Make-up hydrolysis chemicals, as required, pass into line 35 via line 39. Similarly, make-up carboxylic acid passes into line 31 via line 33 and make-up catalyst components pass into line 15 via line 37.

Separation zones 13 and 27 comprise one or more conventional separation units which can contain fractionating columns, absorption towers, adsorption beds,

| Component | Broad | Preferred |
| --- | --- | --- |
| Carboxylic Acid | about 0.1 to about 100 mole/mole | about 1 to about 10 mole/mole |
| Acetic Anhydride | about 0.0 to about 100 mole/mole | about 0.2 to about 10 mole/mole |
| Water | about 0 to about 10 mole/mole | about 0 to about 2 mole/mole |
| Te or Se Compound | about 1 to about 100 millimole/mole | about 10 to about 50 millimole mole |
| Bromide Compound | about 10 to about 1000 millimole/mol | about 150 to about 600 millimole/mole |
| Nitrate Compound | about 1 to about 200 millimole/mole | about 10 to about 100 millimole/mole |

After leaving the reaction zone, the reaction mixture can be separated by conventional methods such as by fractional distillation to isolate and recover the desired products. Incompletely oxidized products can be recycled as well as other components of the reaction mixture which have not been consumed.

In the embodiment in which alkyl-substituted organic feeds are converted to the corresponding aromatic alcohols, the first step is identical with the catalytic oxidation step described earlier. In this step, a substantial portion of a suitable aromatic feed is converted to an ester of the monocarboxylic acid which is present in the oxidation zone. The aromatic ester is separated from the reaction mixture of the catalytic oxidation step and is isolated. It is then subjected to a hydrolysis step wherein the aromatic alcohol is liberated and the monocarboxylic acid is regenerated for recycle to the oxidation step.

Any reaction conditions, including conditions of temperature, time and pressure, which will substantially hydrolyze the ester can be employed. The hydrolysis is readily carried out using excess water and at elevated temperatures, for example, 50–100° C. The hydrolysis is catalyzed by the presence of small amounts of either acids or alkalies. Trace quantities of relatively strong acids such as sulfuric, hydrochloric, trifluoroacetic acid, etc., are effective.

This multi-step embodiment of the present invention is further illustrated by reference to the FIGURE which is a schematic diagram of the process.

In the FIGURE, aromatic feed in line 1 passes into oxidation zone 3 where it contacts, under reaction conditions, catalyst components from line 5, carboxylic acid from line 7, and molecular oxygen from line 9. The reaction effluent from oxidation zone 3 passes via line 11 into separation zone 13. Unconverted aromatic feed, carboxylic acid and catalyst components are returned to oxidation zone 3 via line 15. Oxygenated products such as aldehydes, acids, etc., possibly including some arofilters, etc., as required to carry out the indicated separation. Separation by fractional distillation is generally convenient. Oxidation zone 3 and hydrolysis zone 23 can comprise one or more conventional reactors operating either in parallel or in sequence. The oxidation reaction and the hydrolysis reaction can be carried out either batchwise or continuously.

The products which are obtainable by use of the present invention process are those corresponding to the feedstock wherein the alkyl substituents have been at least partially oxidized to form groups such as alcohol, ketone, aldehyde, acid, or ester groups. The process is particularly effective for producing compounds having alcohol or aldehyde groups. Under the conditions of the reaction the alcohol products are largely in the form of esters which correspond to the specific carboxylic acid present in the reaction zone. When more than one alkyl substituent is present on the feedstock molecule, some or all of these can be oxidized, at least partially, depending upon the severity of the reaction conditions.

The oxygen-containing aromatic products of the present invention have a wide utility. For example, benzoic acid and benzyl alcohol are articles of commerce, being used in various agricultural, pharmaceutical and chemical intermediate applications.

The invention can be further illustrated by the following examples. In each of the examples, batch runs were carried out in a 500 ml glass-lined rocking autoclave. After charging the reactor with the indicated liquid and solid components, the reactor was pressured, except as noted, with 50 psig (at 24° C) initial oxygen pressure.

EXAMPLE I

A series of runs was carried out to illustrate the oxidation of p-tert-butyltoluene. Batch reactions of mixtures having the indicated compositions were subjected to the indicated reaction conditions. After the reaction period, the reaction mixtures were subjected to separations and analysis procedures which included dilution with water, extraction with pentane and analysis of the pentane extract using gas-liquid chromatography, the analyses being reported in area percent. In some instances, the pentane extract was also subjected to fractional distillation. The conversion of the feedstock was computed and the presence of heavy distillation residue, if any, was calculated.

The conditions and results of these runs are shown in Table I below.

TABLE I
Oxygenation of p-tert-Butyltoluene Using Tellurium Compounds

| Run No. | 1 | 2 | 3 | 4 | 5 | 6 | 7 |
|---|---|---|---|---|---|---|---|
| Temp., °C | 150 | 150 | 150 | 160 | 160 | 160 | 160 |
| Time, hrs. | 1.0 | 17.2 | 3.1 | 5.9 | 4.0 | 4.0 | 4.5 |
| Charge | | | | | | | |
| PTBT,[b] moles | 0.19 | 0.19 | 0.19 | 0.19 | 0.19 | 0.19 | 0.19 |
| HOAc, ml | 50 | 50 | 50 | 50 | 50 | 50 | 50 |
| $Ac_2O$, ml | 10 | 10 | 10 | 0 | 0 | 10 | 10 |
| $H_2O$, ml | 0 | 0 | 0 | 3.6 | 3.6 | 0 | 0 |
| $TeO_2$, g | 1 | 1 | 1 | 1 | 1 | 2.5[a] | 2.5[a] |
| LiBr, g | 5 | 5 | 0 | 5 | 5 | 0 | 5 |
| $LiNO_3$, g | 1 | 0 | 1 | 1 | 0 | 1 | 0 |
| Conversion, % | 43 | 9 | 10 | 39 | 1 | 46 | 6 |
| Selectivity, % | | | | | | | |
| Acetate[c] | 72.2 | 62.9 | 48.2 | 58.5 | NA | 47.6 | NA |
| Aldehyde[d] | 8.4 | 27.1 | 27.8 | 17.2 | NA | 28.1 | NA |
| Acid[e] | 5.2 | 0.8 | 0.8 | 12.0 | NA | 13.4 | NA |
| Bromide[f] | 2.6 | 2.4 | 0.0 | 0.4 | NA | 0.4 | NA |
| Alcohol[g] | 1.1 | 0.0 | 0.0 | 3.1 | NA | 2.6 | NA |
| Bromo[h] | 8.5 | 0.0 | 0.0 | 8.7 | NA | 7.0 | NA |
| Other | 2.0 | 6.8 | 9.3 | 0.0 | NA | 1.0 | NA |
| Heavies,[i] % | 0.9 | NA | NA | 1.2 | NA | 2.4 | 60 |

Notes:
[a] $TeBr_4$ used in this run.
[b] p-tert-butyltoluene
[c] p-tert-butylbenzyl acetate
[d] p-tert-butylbenzaldehyde
[e] p-tert-butylbenzoic acid
[f] p-tert-butylbenzyl bromide
[g] p-tert-butylbenzyl alcohol
[h] bromo-p-tert-butyltoluenes
[i] Distillation residue higher boiling than p-tert-butylbenzoic acid.
NA Not available Comparing invention run 1 with control runs 2 and 3 in Table I clearly illustrates that, for best conversion, both a bromide component and a nitrate component should be present in the reaction mixture. Despite the fact that control runs 2 and 3 were reacted for a much longer time than invention run 1, the conversions were far inferior to that of invention run 1.

Comparing invention run 4 with control run 5 illustrates the advantage of the invention catalyst system even in the absence of acetic anhydride and in the presence of a small amount of water. It is again seen that both the bromide and the nitrate should be present for highest conversion. Comparing invention run 4 with invention run 1 also illustrates that operation in the presence of a small amount of water slows down the reaction somewhat and influences the distribution of products, namely, increasing the acid and aldehyde products.

Comparing invention run 6 with control run 7 also illustrates that both a bromide and a nitrate component should be present for best conversion. Invention run 6 shows that tellurium bromide can be used in place of tellurium oxide and that the tellurium compound can be the source of both the required tellurium and bromide components.

EXAMPLE II

Another series of runs was carried out in which toluene and xylene were oxidized using tellurium oxide-containing catalyst systems. These runs were carried out in essentially the same manner as those of Example I. The essential conditions and results of these runs are shown in Table II below.

TABLE II
Oxygenation of Toluene or Xylene Using Tellurium Oxide

| Run No. | 1 | 2 | 3 | 4 | 5 | 6 |
|---|---|---|---|---|---|---|
| Temp. °C | 160 | 100 | 150[a] | 150 | 160 | 160 |
| Time, hrs. | 4.8 | 4.0 | 17.8 | 22.3 | 2.0 | 1.0 |
| Charge | | | | | | |
| Tol., moles | 0.19 | 0.19 | 0.19 | 0.19 | 0.19 | 0.19[c] |
| HOAc, ml | 50 | 50 | 50 | 50 | 50 | 50 |
| $Ac_2O$, ml | 10 | 0 | 10 | 10 | 0 | 10 |
| $H_2O$, ml | 0 | 0 | 0 | 0 | 3.1[b] | 0 |
| $TeO_2$, g | 1 | 1.2 | 1 | 1 | 1.2 | 1 |
| LiBr, g | 5 | 10 | 2.5 | 2.5 | 0 | 5 |
| $LiNO_3$, g | 1 | 1 | 1 | 0 | 1 | 1 |
| Conversion, % | 49 | 54 | 26 | 6 | 47 | 44 |
| Selectivity, %[i] | | | | | | |
| Acetate | 76.0 | 18.7 | 69.5 | 39.2 | 70.0 | 56.8[d] |
| Aldehyde | 7.0 | 0.0 | 12.6 | 11.5 | 11.9 | 4.9[e] |
| Acid | 0.4 | 0.0 | 1.6 | 0.0 | 4.4 | 0.0 |
| Bromide | 0.8 | 19.0 | 0.0 | 0.0 | 1.7 | 2.9[f] |
| Alcohol | 0.6 | 0.0 | 1.7 | 26.2 | 0.0 | 0.5[g] |
| Bromo | 8.9 | 59.8 | 8.2 | 0.0 | 8.8 | 26.7[h] |
| Other | 6.3 | 2.5 | 6.4 | 23.1 | 3.2 | 8.2 |
| Heavies, %[j] | 1.4 | 1.5 | NA | NA | 1.9 | 4.0 |

Notes:
[a] Initial $O_2$ pressure was 64 psig at 24° C. All others were 50 psig.
[b] 48 wt.% HB solution
[c] p-xylene. All others were toluene.
[d] p-methylbenzyl acetate
[e] p-methylbenzaldehyde
[f] p-methylbenzyl bromide
[g] p-methylbenzyl alcohol
[h] bromo-p-xylenes
[i] Oxygenated products of toluene are benzyl acetate, benzaldehyde, benzoic acid, benzyl bromide, benzyl alcohol, bromotoluenes, respectively.
[j] Distillation residue higher boiling than aromatic acid.

Invention runs 1, 2 and 3 of Table II illustrate that the process of the present invention is effective for converting toluene to oxygenated products in high conversion and high selectivity. Comparing inventive runs 2 and 3 with invention run 1 shows that the distribution of products, as well as the level of conversion can be significantly influenced by changes in reaction conditions including decreasing the reaction temperature and increasing or reducing the amount of bromide component in the reaction mixture, or by operating in the absence of acetic anhydride. A comparison of invention run 3 with control run 4 again shows that, for best conversion, both a bromide component and a nitrate component should be present in the reaction zone.

Invention run 5 shows that hydrogen bromide is a suitable alternative for lithium bromide in the invention catalyst system. Invention run 6 shows that the invention process is also applicable for the oxygenation of p-xylene.

EXAMPLE III

In a manner similar to that of preceding Examples I and II, a number of runs were carried out in which toluene was oxidized using a selenium oxide-containing catalyst system. The essential conditions and results of these runs are shown in Table III on the following page.

TABLE III

| | Oxygenation of Toluene Using Selenium Oxide | | | | |
|---|---|---|---|---|---|
| Run No. | 1 | 2 | 3 | 4 | 5 |
| Temp., ° C | 150 | 150 | 150 | 150 | 190–200 |
| Time, hrs. | 1.0 | 4.6 | 3.3 | 2.5 | 4.0 |
| Charge | | | | | |
| Tol., moles | 0.19 | 0.19 | 0.19 | 0.19 | 0.19 |
| HOAc, ml | 50 | 50 | 50 | 50 | 50 |
| Ac$_2$O, ml | 10 | 10 | 0 | 0 | 0 |
| H$_2$O, ml | 0 | 0 | 0 | 5 | 5 |
| SeO$_2$, g | 1 | 1 | 1 | 1 | 1 |
| LiBr, g | 5 | 5 | 0 | 5 | 5 |
| LiNO$_3$, g | 1 | 0 | 5 | 1 | 0 |
| Conversion, % | 35 | 0 | 13 | 48 | 20 |
| Selectivity, %$^a$ | | | | | |
| Acetate | 32.6 | NA | 27.0 | 49.6 | 30.6 |
| Aldehyde | 4.1 | NA | 12.7 | 14.2 | 6.8 |
| Acid | 1.3 | NA | 45.3 | 2.5 | 2.0 |
| Bromide | 8.4 | NA | 0.0 | 0.1 | 0.7 |
| Alcohol | 0.0 | NA | 8.7 | 0.2 | 1.6 |
| Bromo | 46.8 | NA | 0.0 | 31.3 | 51.5 |
| Other | 6.8 | NA | 6.3 | 2.2 | 6.8 |

$^a$Oxygenated products are as shown in Table II.

Comparison of invention run 1 with control runs 2 and 3 in Table III again show that for best conversions and selectivity to oxygenated products, both a bromide component and a nitrate component should be present in the reaction mixture. Invention run 4 shows that the combination of a bromide component and a nitrate component is also effective in a system in which acetic anhydride is absent and a small amount of water is present. Control run 5 again shows that the nitrate component is necessary for best conversions and that a high reaction temperature cannot compensate for its absence.

EXAMPLE IV

The following calculated example is presented to further illustrate the two step embodiment of the invention to produce benzyl alcohol by employing both an oxidation step and a hydrolysis step.

In a combination process generally as depicted in the FIGURE, a glass lined, stirred reactor in oxidation zone 3 is charged with 1,000 moles toluene, 4,700 moles acetic acid, 39.5 moles TeO$_2$, a solution of 145 moles HBr in 700 moles H$_2$O, and 79 moles LiNO$_3$. The reactor is then pressured with sufficient oxygen to provide an oxygen partial pressure of 50 psig within the reactor, then heated to 160° C and maintained at that temperature for 120 minutes.

The reactor contents are then passed into separation zone 13 containing a series of fractionating columns from which are recovered 329 moles benzyl acetate and 141 moles of a mixture of by-products comprising benzaldehyde, benzoic acid, bromotoluenes, and benzyl bromides. About 4341 moles of acetic and 530 moles of toluene are also recovered and returned to oxidation zone 3.

The 329 moles of benzyl acetate from separation zone 13 are conducted to a stirred stainless steel reactor in hydrolysis zone 23 and contacted with 5000 moles water and 5 moles sulfuric acid for 80 minutes at 75° C and at 25 psig.

The effluent from the hydrolysis reactor is passed into separation zone 27 containing a series of fractionators from which are recovered 319 moles of benzyl alcohol product. Also recovered are 319 moles of acetic acid which are passed back to the reactor in oxidation zone 3 where it is combined with 40 moles of make-up acetic acid and the 4341 moles of acetic acid returned from separation zone 13 to make up the 4700 mole charge for the reactor in oxidation zone 3.

We claim:

1. A process for oxygenating an alkyl-substituted aromatic compound of the formula

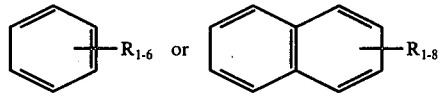

wherein each R is selected from branched or unbranched alkyl groups having from one to about 6 carbon atoms, at least one R being an alkyl group free of quaternary carbon atoms, comprising a liquid phase and elevated temperature contacting of said compound with molecular O$_2$ in the presence of an alkanoic acid having from 1 to about 6 carbon atoms per molecule, an at least partially soluble Te or Se compound, an inorganic bromine compound, and a compound selected from inorganic nitrates and compounds convertible to inorganic nitrates at conditions of the present process said compounds selected from the group consisting of alkali metal nitrates, nitric acids, and oxides of nitrogen.

2. A process according to claim 1 which is carried out in two distinct steps:
   a. contacting said alkyl-substituted aromatic compound with molecular O$_2$, said carboxylic acid, said Te or Se compound, and said inorganic bromine compound, in the presence of an inorganic nitrate compound to produce an ester comprising both an aromatic alcohol and said carboxylic acid; and
   b. hydrolyzing said ester to produce an aromatic alcohol and to regenerate the carboxylic acid.

3. A process of claim 1 wherein said carboxylic acids are present in the range of about 0.1 to about 100 moles per mole of alkyl-substituted aromatic feedstock.

4. A process of claim 1 wherein said tellurium and selenium compounds are selected from among tellurium dioxide, tellurium tetrabromide, and selenium dioxide.

5. A process of claim 4 wherein said tellurium and selenium compounds are present in the range of about 1 to about 100 millimoles per mole of alkyl-substituted aromatic feedstock.

6. A process of claim 1 wherein said bromide component is selected from among alkali metal bromides and hydrogen bromide.

7. A process of claim 6 wherein said bromide compounds are present in the range of about 10 to about 1000 millimole per mole of alkyl-substituted aromatic feedstock.

8. A process of claim 1 wherein the concentration of nitrate compound contacted with the alkyl-substituted aromatic compound is in the range of from about 1 to about 200 millimole per mole of alkyl-substituted aromatic feedstock.

9. A process of claim 1 wherein the reaction conditions are those conditions of temperature and pressure under which the reaction mixture is substantially in the liquid phase.

10. A process of claim 9 wherein the temperature is maintained within the range of about 50° to about 200° C and the partial pressure of oxygen in the system is within the range of about 5 to about 500 psig.

* * * * *